(12) United States Patent
Bian et al.

(10) Patent No.: US 11,175,490 B1
(45) Date of Patent: Nov. 16, 2021

(54) SHUTTER-TYPE ADAPTIVE THREE-DIMENSIONAL DISPLAY SYSTEM BASED ON MEDICAL MICROSCOPIC IMAGING

(71) Applicant: INSTITUTE OF AUTOMATION, CHINESE ACADEMY OF SCIENCES, Beijing (CN)

(72) Inventors: Guibin Bian, Beijing (CN); Jinlian Song, Beijing (CN); Wenhao He, Beijing (CN); Zhen Li, Beijing (CN); Haitao Song, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/322,926

(22) Filed: May 18, 2021

(30) Foreign Application Priority Data

Nov. 10, 2020 (CN) .......................... 202011243537.2

(51) Int. Cl.
  *H04N 7/18* (2006.01)
  *G02B 21/36* (2006.01)
  (Continued)

(52) U.S. Cl.
  CPC .......... *G02B 21/367* (2013.01); *G02B 30/24* (2020.01); *H04N 13/128* (2018.05);
  (Continued)

(58) Field of Classification Search
  CPC .... G02B 21/367; G02B 30/24; H04N 13/128; H04N 13/239; H04N 13/341;
  (Continued)

(56) References Cited

U.S. PATENT DOCUMENTS

| 9,030,535 B2 * | 5/2015 | Kim | ...................... H04N 13/139 348/53 |
| 2012/0098830 A1 * | 4/2012 | Kim | ...................... H04N 13/341 345/419 |

FOREIGN PATENT DOCUMENTS

| CN | 2860384 Y | 1/2007 |
| CN | 102566027 A | 7/2012 |

(Continued)

*Primary Examiner* — Shan E Elahi

(74) *Attorney, Agent, or Firm* — Bayramoglu Law Offices LLC

(57) ABSTRACT

A shutter-type adaptive three-dimensional (3D) display system based on medical microscopic imaging is provided. In the system, a binocular camera is connected to an operating microscope optical system through a beam splitter, and is configured to acquire binocular image data. A control module is configured to input control instructions, where the control instructions include a first type of control instructions and a second type of control instructions. An image processing module calculates image parallaxes based on the binocular image data under the first type of control instructions, and transmits the image parallaxes to the binocular camera to adjust offsets. A display module is configured to generate display data based on the binocular image data and display the display data through a display device for viewing with 3D glasses. The operating microscope optical system is configured to perform an adjustment based on the control instructions.

4 Claims, 4 Drawing Sheets

(51) Int. Cl.
  *G02B 30/24* (2020.01)
  *H04N 13/239* (2018.01)
  *H04N 13/296* (2018.01)
  *H04N 13/341* (2018.01)
  *H04N 13/128* (2018.01)
  *H04N 13/167* (2018.01)
  *H04N 13/00* (2018.01)

(52) U.S. Cl.
  CPC ......... *H04N 13/167* (2018.05); *H04N 13/239* (2018.05); *H04N 13/296* (2018.05); *H04N 13/341* (2018.05); *H04N 2013/0081* (2013.01); *H04N 2213/008* (2013.01)

(58) Field of Classification Search
  CPC ............... H04N 13/296; H04N 13/167; H04N 2013/0081; H04N 2213/008
  USPC .......................................................... 348/47
  See application file for complete search history.

(56) References Cited

FOREIGN PATENT DOCUMENTS

| | | | | |
|---|---|---|---|---|
| CN | 104618707 | A | 5/2015 | |
| CN | 107710756 | A | 2/2018 | |
| CN | 108470324 | A | 8/2018 | |
| CN | 111788508 | A | 10/2020 | |
| CN | 112068300 | A * | 12/2020 | ............. G02B 30/24 |

\* cited by examiner

SHUTTER-TYPE ADAPTIVE THREE-DIMENSIONAL DISPLAY SYSTEM BASED ON MEDICAL MICROSCOPIC IMAGING

CROSS REFERENCE TO THE RELATED APPLICATIONS

This application is based upon and claims priority to Chinese Patent Application No. CN 202011243537.2, filed on Nov. 10, 2020, the entire contents of which are incorporated herein by reference.

TECHNICAL FIELD

The present invention belongs to the field of microscopic imaging, and more particularly, relates to a shutter-type adaptive three-dimensional (3D) display system based on medical microscopic imaging.

BACKGROUND

As a common instrument in the life science research field, microscopes are widely used in multidisciplinary scientific research and practice such as pathology, clinical medicine, pharmacology, and authentication of traditional Chinese medicine. With the continuous improvement of the medical level and the increasingly complex and diverse clinical needs, more and more delicate operations, inspections and teaching experiments are carried out with the help of microscopes. The operation under the microscope is delicate and time-consuming in a limited operative field, and it requires the doctor to look at the microscope for a long time with high attention. As a result, the doctor will inevitably suffer from physical and mental discomfort such as eyestrain and neck fatigue, which may affect the operation and even may lead to a medical accident. Meanwhile, it is difficult to explain the teaching experiment under the microscope, and it is difficult to realize real-time observation by two or more persons during the explanation process, which greatly reduces the teaching efficiency and learning effect.

In order to alleviate the fatigue of the doctor during the operation and to ensure the safety of the operation and improve the teaching effect under the microscope, it is very important to study a three-dimensional (3D) display system that mimics and replaces human eyes to observe the target through the eyepiece. However, the image parallaxes acquired by the left and right cameras will affect the 3D display quality and easily cause visual fatigue of the human eyes. At present, the image parallaxes may be adjusted by mounting a position sensor on the microscope. This method requires modification of the microscope body, which is not universally applicable; it also needs to calibrate the position sensor point-by-point according to the distance between the microscope body and the target, which is difficult to operate and complex to calibrate. The image parallaxes may also be adjusted by using a traditional image matching algorithm. However, it is hard to achieve high frame rate processing, and it is prone to point mismatching, slow processing speed and poor robustness. In addition, the continuous running of the algorithm during the operation will reduce the safety of the operation. Therefore, it is necessary to overcome the shortcomings of poor universality and complex operation in adjusting the image parallaxes by a hardware and the shortcomings of slow speed, poor robustness, and low safety in adjusting the image parallaxes by a traditional algorithm. To this end, the present invention provides a shutter-type adaptive 3D display system based on medical microscopic imaging, which can improve the comfort of the doctor in the operation under the microscope to avoid a medical accident, and can also improve the convenience and efficiency of the teaching experiment under the microscope and reduce the teaching difficulty.

SUMMARY

In order to solve the above problems in the prior art, that is, the poor universality and complex operation in adjusting the image parallaxes by a hardware and the slow speed and poor robustness in adjusting the image parallaxes by an algorithm, the present invention provides a shutter-type adaptive three-dimensional (3D) display system based on medical microscopic imaging. The system includes an operating microscope optical system, a beam splitter, a binocular camera, a control module, an image processing module and a display module.

The binocular camera is connected to the operating microscope optical system through the beam splitter, and is configured to acquire binocular image data.

The control module is configured to input control instructions. The control instructions include a first type of control instructions and a second type of control instructions.

The image processing module calculates image parallaxes based on the binocular image data under the first type of control instructions, and transmits the image parallaxes to the binocular camera to adjust offsets.

The display module is configured to generate display data based on the binocular image data and display the display data through a display device for viewing with 3D glasses.

The operating microscope optical system is configured to perform an adjustment based on the control instructions.

In some preferred embodiments, the system may further include shutter-type 3D glasses, and the display device is a shutter-type 3D display screen.

In some preferred embodiments, the control module is a pedal switch module, and the pedal switch module include directional pedals and focusing pedals.

In some preferred embodiments, the directional pedals include six pedals, namely a moving-up pedal, a moving-down pedal, a translating-left pedal, a translating-right pedal, a translating-forward pedal and a translating-backward pedal. The focusing pedals include two pedals, namely a zooming-in pedal and a zooming-out pedal.

In some preferred embodiments, the first type of control instructions include moving up, moving down, zooming in and zooming out. The second type of control instructions include translating left, translating right, translating forward and translating backward.

In some preferred embodiments, the image processing module calculates the image parallaxes based on the binocular image data by a method including:

zooming out left and right images in the binocular image data by an identical multiple;

extracting and describing feature points of the zoomed-out left and right images;

eliminating mismatched feature points of the zoomed-out left and right images to obtain final matching points; and calculating the image parallaxes based on the final matching points.

In some preferred embodiments, the mismatched feature points of the zoomed-out left and right images are eliminated by using an improved grid-based motion statistics (IGMS) algorithm including:

performing high-quantity matching on the zoomed-out left and right images by using a brute force (BF) matching algorithm based on the extracted feature points;

roughly eliminating mismatched points by primarily using a GMS algorithm, and selecting first n matching points with a high matching degree; and finely eliminating mismatched points in the selected first n matching points by secondarily using the GMS algorithm; where, n is a preset value.

In some preferred embodiments, the step of extracting and describing the feature points of the zoomed-out left and right images is performed by using an oriented features from accelerated segment test (FAST) and rotated binary robust independent elementary features (BRIEF) (ORB) algorithm.

In some preferred embodiments, a method for calculating the image parallaxes includes:

calculating average coordinate differences $P_x, P_y$ of the final matching points of the zoomed-out left and right images, and converting the average coordinate differences into image parallaxes $aP_x, bP_y$, where a, b are preset parameters.

In some preferred embodiments, the display module generates the display data based on the binocular image data and display the display data through the display device for viewing with the 3D glasses by a method including:

compressing the left and right images in the binocular image data by half in a width direction to fully fill left and right screens of the display device, respectively.

The present invention has the following advantages.

The image processing module of the present invention works only under the first type of control instructions. In this way, when the image parallaxes change, the image processing module can calibrate the parallaxes in real time to ensure viewing comfort. When the image parallaxes do not change, the image processing module can stop running to ensure absolute safety in the operation.

The present invention improves the 3D display quality by conveniently and quickly adjusting the image parallaxes. The present invention can relieve the physical and mental discomfort of the doctor's eyestrain and neck fatigue in the long-term delicate operation under the microscope, thereby improving the operation effect and reducing medical accidents. In addition, the present invention can realize real-time observation by multiple people in the teaching experiment under the microscope, thereby improving the teaching efficiency and learning effect. The present invention can be used in life science research fields such as microsurgery, pathology and clinical medicine as well as teaching experiments under the microscope.

BRIEF DESCRIPTION OF THE DRAWINGS

Other features, objectives and advantages of the present invention will become more apparent upon reading the detailed description of the non-restrictive embodiments with reference to the following drawings.

DETAILED DESCRIPTION OF THE EMBODIMENTS

Figure 1:
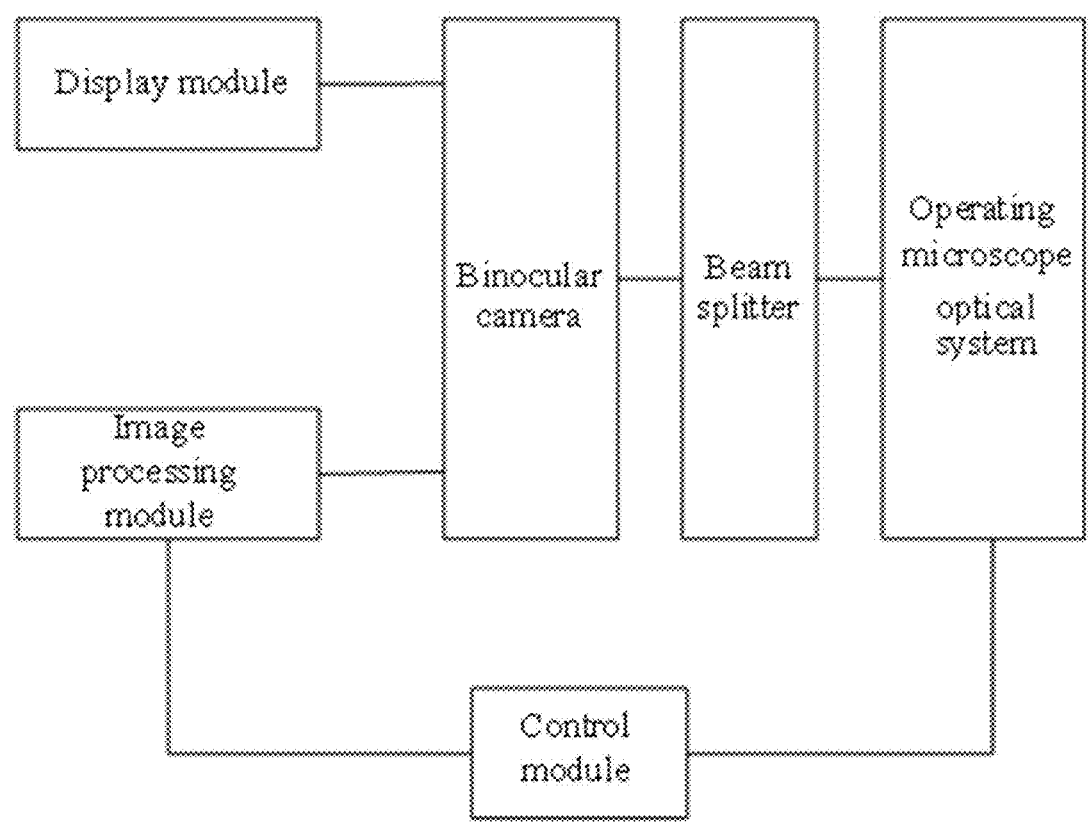
FIG. 1 is a block diagram of a shutter-type adaptive three-dimensional (3D) display system based on medical microscopic imaging according to an embodiment of the present invention.

In order to make the objectives, technical solutions, and advantages of the present invention clearer, the technical solutions in the embodiments of the present invention will be described clearly and completely in conjunction with the drawings. Obviously, the described embodiments are parts of the embodiments of the present invention, rather than all of the embodiments. Based on the embodiments of the present invention, all other embodiments obtained by those skilled in the art without creative work shall fall within the scope of protection of the present invention.

The present invention will be further described in detail below with reference to the drawings and embodiments. It can be understood that the specific embodiments described here are only used to explain the related invention, but not to limit the invention. In addition, it should be noted that, for ease of description, only the parts related to the relevant invention are shown in the drawings.

It should be noted that the embodiments in the present invention and the features in the embodiments can be combined with each other if there is no conflict.

As shown in FIG. 1, a shutter-type adaptive three-dimensional (3D) display system based on medical microscopic imaging according to the present invention includes an operating microscope optical system, a beam splitter, a binocular camera, a control module, an image processing module, and a display module.

The binocular camera is connected to the operating microscope optical system through the beam splitter, and is configured to acquire binocular image data.

The control module is configured to input control instructions, where the control instructions include a first type of control instructions and a second type of control instructions.

The image processing module calculates image parallaxes based on the binocular image data under the first type of control instructions, and transmits the image parallaxes to the binocular camera to adjust offsets.

The display module is configured to generate display data based on the binocular image data and display the display data through a display device for viewing with 3D glasses.

The operating microscope optical system is configured to perform an adjustment based on the control instructions.

In order to more clearly describe the shutter-type adaptive 3D display system based on medical microscopic imaging provided by the present invention, various parts in a preferred embodiment of the present invention are described in detail below with reference to the drawings.

Figure 2:
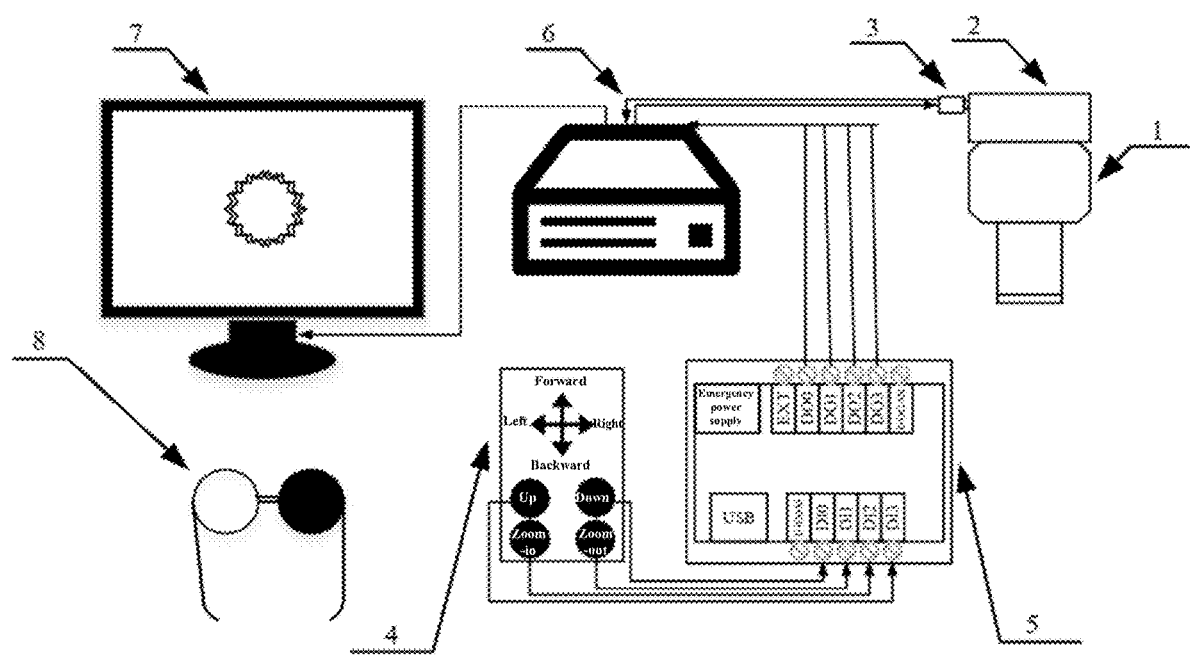
FIG. 2 is a schematic diagram of the shutter-type adaptive 3D display system based on medical microscopic imaging according to another embodiment of the present invention.

As shown in FIG. 2, the shutter-type adaptive 3D display system based on medical microscopic imaging according to an embodiment includes the operating microscope optical system 1, the beam splitter 2, the binocular camera 3, the control module 4, the industrial input/output (I/O) control card 5, the image processing module 6, the image 3D display module 7, and the shutter-type 3D glasses 8. In an embodiment, the image processing module 6 is mounted in a host computer. The host computer, as an information interaction center, is connected to the image 3D display module 7, the industrial I/O control card 5 and the binocular camera 3 to transmit information of each part.

The operating microscope optical system 1 is configured to perform clear imaging at different zoom ratios, and allow light to enter the binocular camera 3 through the beam splitter 2 for acquiring binocular images. The binocular camera 3 is used to imitate human eyes for acquiring images.

The control module 4 is a pedal switch module, and is configured to control the operating microscope optical system 1 to adjust a position and a zoom ratio. The adjustment of the position includes translating forward, translating backward, translating left, translating right, moving up and moving down. The adjustment of the zoom ratio includes zooming in and zooming out.

The industrial I/O control card 5 is configured to receive a switch quantity signal of the pedal switch module, and feeds back the signal to the image processing module in real time to control the operation and stop of the image processing module.

The image processing module 6 is configured to quickly and adaptively calibrate image parallaxes of the binocular camera to ensure the viewing comfort.

The image 3D display module 7 is configured to horizontally compress images acquired by left and right cameras of the binocular camera and separately display the images on left and right sides of the shutter-type 3D display screen for image fusion, so that a user can view the images through the shutter-type 3D glasses 8.

In an embodiment, the operating microscope optical system 1 includes a primary lens capable of presenting an image with excellent three-dimensionality and microscopic details, a wide-field-of-view eyepiece, and a multi-layer anti-reflective and apochromatic large-flat field objective lens, which can achieve high-quality microscopic imaging. The beam splitter 2 is mounted on the operating microscope optical system 1, and the binocular camera 3 is mounted on the beam splitter 2. In this way, the received light can be reflected by the beam splitter 2 to the binocular camera 3 to form left and right images. The formed left and right images are transmitted to the image processing module 6 for parallax calculation, and a photographing area of the binocular camera 3 is controlled according to a parallax parameter. The images acquired by the binocular camera 3 are transmitted to the image 3D display module 7 for display for viewing by a user with the shutter-type 3D glasses 8. When the image processing module 6 is started and stopped, the industrial I/O control card 5 receives the switching signals of the pedal switch module to perform the control.

Figure 3:
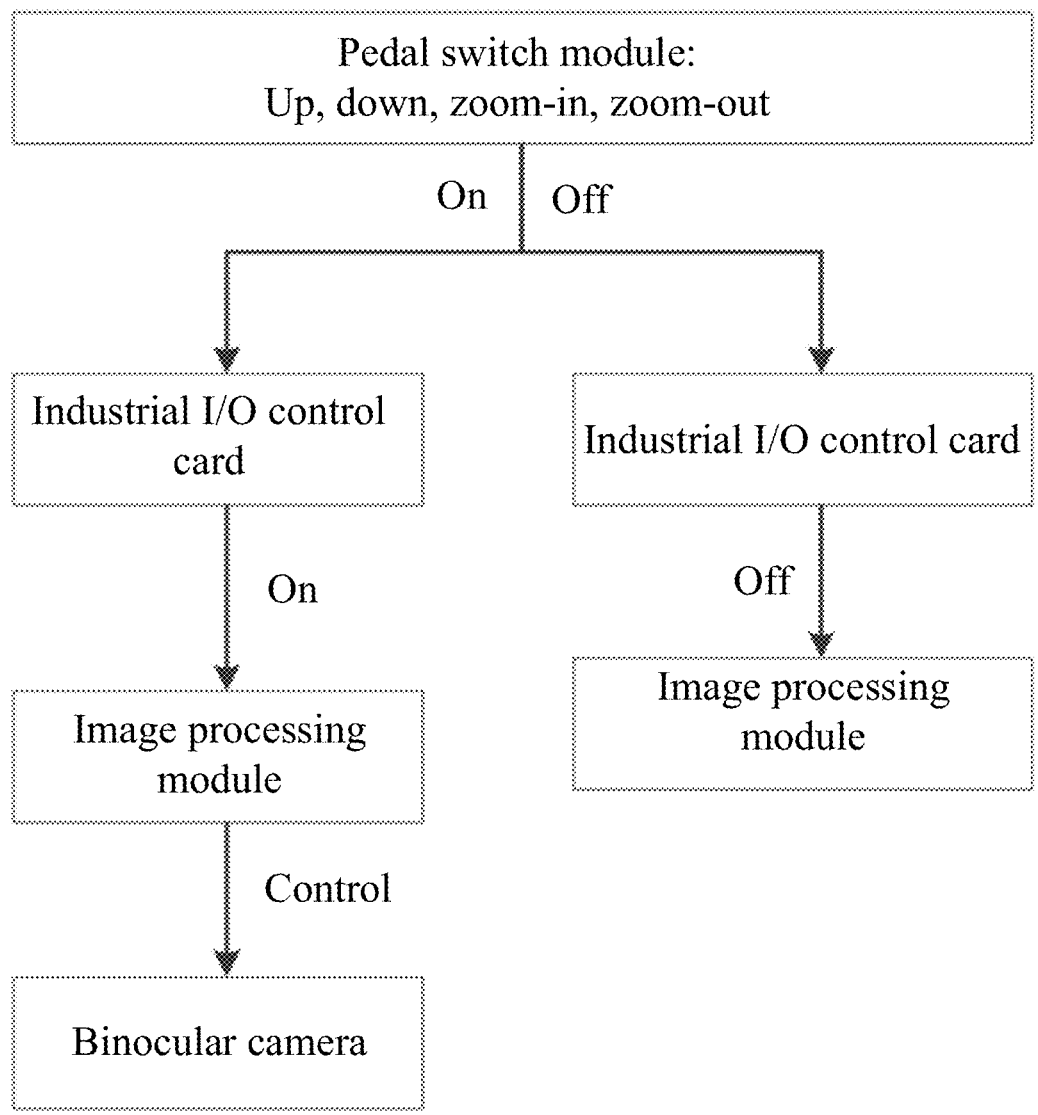
FIG. 3 is a flowchart of a method for starting and stopping an image processing module according to an embodiment of the present invention.

The pedal switch module can control the operating microscope optical system 1 to move up, down, left, right, forward and backward and to zoom in and out by means of directional pedals and focusing pedals provided on the pedal switch module. Since the left, right, forward and backward movement (the second type of control instructions) of the operating microscope optical system 1 do not affect the change of the parallax of the left and right images, the industrial I/O control card 5 does not need to receive these four signals. As shown in FIG. 3, only when the pedal switch module controls the operating microscope optical system 1 to move up and down and to zoom in and out (the first type of control instructions), the industrial I/O control card 5 receives the signals of the pedal switch module and activates the image processing module 6 to process the acquired images in real time. After the image parallaxes are obtained, the offsets of the binocular camera are adjusted to ensure adaptive and real-time adjustment of the image parallax. The images acquired by the binocular camera after the parallax is adjusted are transmitted to the image 3D display module 7 in real time for display, so as to maintain the viewing comfort. When the switch of the pedal switch module used to control the operating microscope optical system 1 to move up and down and to zoom in and out is turned off, the left and right images match to the optimal display state. At this time, the industrial I/O control card 5 receives a stop signal from the pedal switch module, and transmits the signal to the image processing module 6 to stop adjusting the image parallax. In this way, absolute safety can be guaranteed during an operation, and a potential risk caused by the running of the program can be avoided. The image data acquired by the binocular camera 3 is directly transmitted to the image 3D display module 7, and the image 3D display module 7 converts the image into display data and displays the display data for viewing with the 3D glasses.

Figure 4:
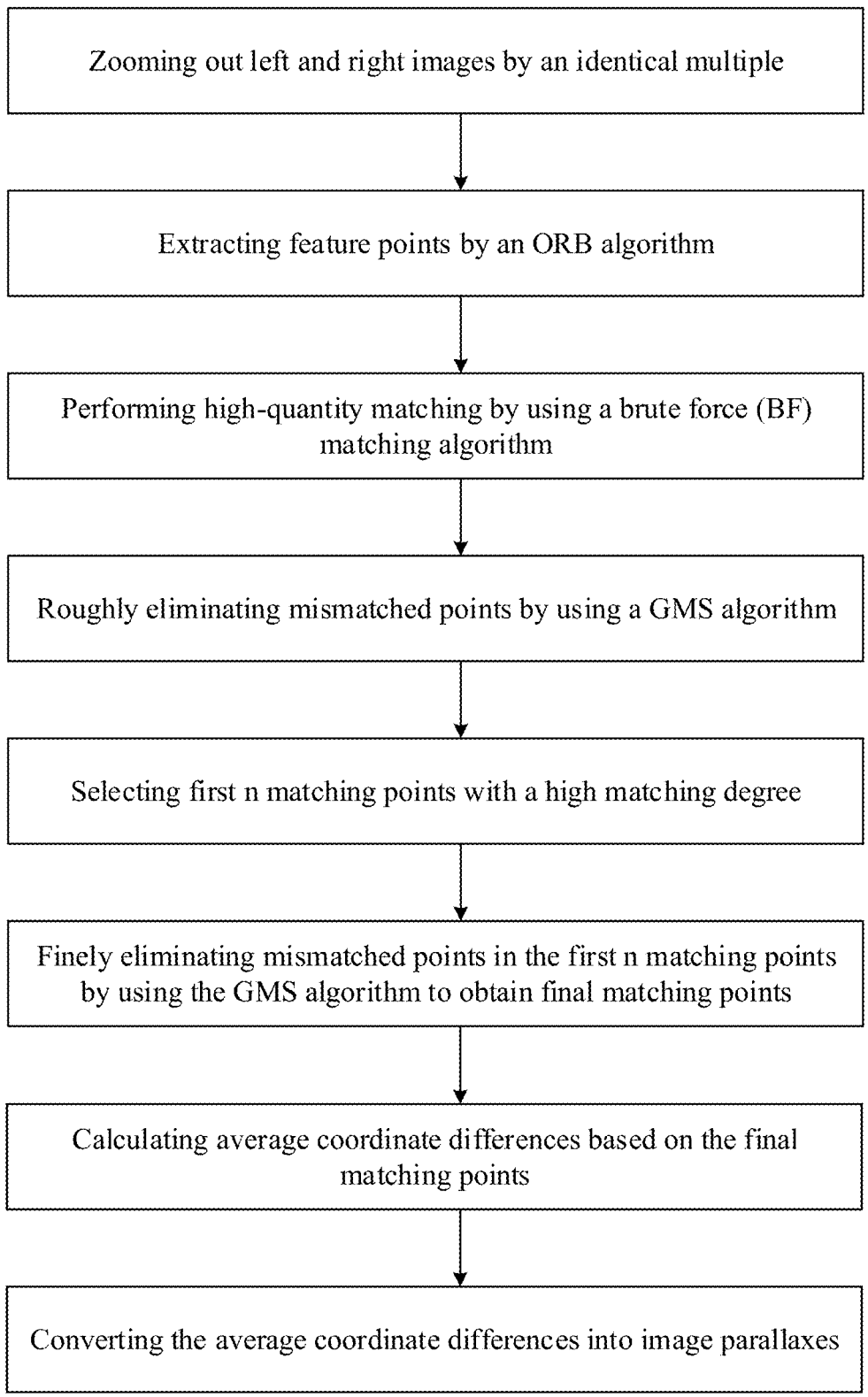
FIG. 4 is a flowchart of a method for calculating image parallaxes according to an embodiment of the present invention.

In an embodiment, as shown in FIG. 4, a method for calculating the image parallaxes based on the binocular image data by the image processing module includes the following steps.

(1) Image Data Acquisition

The image data here is binocular image data, which is acquired by the binocular camera. Two industrial cameras or a binocular camera product may be employed. When image acquisition is performed, parameters of the left and right cameras such as resolution, exposure time and frame rate are consistently set to ensure an absolute level of the left and right cameras, where the frame rate is set to be larger than 60 f/s.

(2) Image Matching

First, the left and right images $F_L(x,y), F_R(x,y)$ acquired by the binocular camera are zoomed out by an identical multiple to quickly extract the feature. Let the size of the processed image to be ω×h:

$$\omega = \frac{W}{a}, h = \frac{H}{b}$$

where, W×H is the size of the original images; a and b are a zoom factor of a width and a zoom factor of a height of images, respectively.

Then, feature points of the zoomed-out left and right images are extracted and described by an oriented features from accelerated segment test (FAST) and rotated binary robust independent elementary features (BRIEF) (ORB) algorithm.

Finally, mismatched feature points of the zoomed-out left and right images are eliminated by an improved grid-based motion statistics (IGMS) algorithm to obtain final matching points. This algorithm is fast and robust, and can improve the stability of matching.

In an embodiment, the IGMS algorithm is as follows:

1) High-quantity matching is performed on the zoomed-out left and right images by using a brute force (BF) matching algorithm based on the extracted feature points.

2) Mismatched points are roughly eliminated by primarily using a grid-based motion statistics (GMS) algorithm, and first n matching points with a high matching degree are selected.

3) Mismatched points in the selected first n matching points are then finely eliminated by secondarily using the GMS algorithm, where 10≤n≤20.

(3) Image Parallaxes

Average coordinate differences $P_x, P_y$ of the final matching points of the zoomed-out left and right images are calculated, and converted into image parallaxes $aP_x, bP_y$. The image parallaxes are transmitted to the camera in real time to control offsets of the left and right cameras in directions x, y.

In an embodiment, the image 3D display module includes image processing and 3D display. Specifically, the left and right images in the binocular image data are compressed by half in a width direction, respectively, and then the zoomed-out left and right images fully fill left and right screens of the display screen, respectively. The display screen is a shutter-type display screen with a refresh rate of 120 Hz, and needs to be used with the shutter-type 3D glasses 8.

In particular, according to the embodiments of the present invention, the related content of the steps of the method may be implemented as a computer software program. For example, an embodiment of the present invention provides a computer program product, which includes a computer program carried by a computer-readable medium. The computer program includes program code for executing the method shown in the flowchart. In this embodiment, the computer program may be downloaded from a network by means of the communication part and be installed, and/or be installed from the removable medium. When the computer program is executed by a central processing unit (CPU), the functions defined in the method of the present invention are executed. It should be noted that the computer-readable medium in the present invention may be a computer-readable signal medium, or a computer-readable storage medium, or a combination of the computer-readable signal medium and the computer-readable storage medium. For example, the computer-readable storage medium may be, but is not limited to, electric, magnetic, optical, electromagnetic, infrared, or semiconductor system, apparatus or device, or any combination of the above. Specifically, for example, the computer-readable storage medium may include, but is not limited to: an electric connector with one or more wires, a portable computer magnetic disk, a hard drive, a random access memory (RAM), a read-only memory (ROM), an erasable programmable read-only memory (EPROM or flash drive), an optical fiber, a compact disk read-only memory (CD-ROM), an optical storage device, a magnetic storage device, or any proper combination of the above. In the present invention, the computer-readable storage medium may be any tangible medium containing or storing a program, and the program may be used by or used in combination with an instruction execution system, apparatus or device. In the present invention, the computer-readable signal medium may include a data signal propagated in a baseband or propagated as a part of a carrier, and carries computer-readable program code. Such a propagated data signal may be in multiple forms, including, but not limited to an electromagnetic signal, an optical signal, or any proper combination of the above. The computer-readable signal medium may also be any computer-readable medium except the computer-readable storage medium. The computer-readable storage medium may send, propagate or transmit a program used by or used in combination with an instruction execution system, apparatus or device. The program code contained on the computer-readable medium may be transmitted by using any suitable medium, including, but not limited to radio, an electric wire, an optical fiber radio frequency (RF) and others, or any proper combination of the above.

Computer program code for executing the operations in the present invention may be compiled by using one or more programming languages or a combination thereof. The programming languages include object-oriented programming languages, such as Java, Smalltalk, and C++, and conventional procedural programming languages, such as C or similar programming languages. The program code can be executed fully on a user computer, executed partially on a user computer, executed as an independent software package, executed partially on a user computer and partially on a remote computer, or executed fully on a remote computer or a server. In a circumstance in which a remote computer is involved, the remote computer may be connected to a user computer via any type of network, including a local area network (LAN) or a wide area network (WAN), or may be connected to an external computer (for example, connected via the Internet by using an Internet service provider).

The flowcharts and block diagrams in the drawings illustrate system architectures, functions and operations that may be implemented by the system, method and computer program product according to the embodiments of the present invention. In this regard, each block in the flowcharts or block diagrams may represent a module, a program segment or a part of code, and the module, the program segment or the part of code includes one or more executable instructions for implementing specified logic functions. It should also be noted that, in some alternative implementations, functions marked in the blocks also may be implemented in an order different from the order marked in the drawings. For example, two connected blocks may actually be executed substantially in parallel, and may be executed in a reverse order sometimes, which depends on involved functions. It should also be noted that each block in the flowcharts and/or block diagrams and combinations of the blocks in the flowcharts and/or block diagrams may be implemented by a special hardware-based system for executing specified functions or operations, or may be implemented by a combination of special hardware and computer instructions.

The terms "first", "second", etc. are used to distinguish similar objects, rather than to describe or indicate a specific order or sequence.

The term "include/comprise" or any other similar term refers to a non-exclusive inclusion, so that a process, method, article or equipment/apparatus including a series of elements includes not only those elements, but also other elements not explicitly listed, or also includes the inherent elements of the process, method, article or equipment/apparatus.

Hereto, the technical solutions of the present invention have been described in conjunction with the preferred embodiments shown in the drawings. However, those skilled in the art will readily understand that the scope of protection of the present invention is obviously not limited to these specific embodiments. Without departing from the principle of the present invention, those skilled in the art can make equivalent changes or replacements to the relevant technical features, and the technical solutions obtained after these changes or replacements shall fall within the scope of protection of the present invention.

What is claimed is:

1. A shutter type adaptive three-dimensional (3D) display system based on a medical microscopic imaging, comprising:
    an operating microscope optical system;
    a beam splitter;
    a binocular camera;
    a control module;
    an image processing module;
    a display module, and
    an industrial input/output (I/O) control card, wherein the binocular camera is connected to the operating microscope optical system through the beam splitter, and the binocular camera is configured to acquire binocular image data;

the control module is configured to input control instructions, wherein the control instructions comprise a first type of control instructions and a second type of control instructions;

the control module is a pedal switch module;

the pedal switch module comprises directional pedals and focusing pedals;

wherein the first type of control instructions comprise moving up, moving down, zooming in and zooming out; and the second type of control instructions comprise translating left, translating right, translating forward and translating backward;

the image processing module calculates image parallaxes based on the binocular image data under the first type of control instructions, and the image processing module transmits the image parallaxes to the binocular camera to adjust offsets;

wherein a method for calculating the image parallaxes specifically comprises:

acquiring the binocular image data;

zooming out left binocular image data and right binocular image data $F_L(x, y), F_R(x, y)$ in the binocular image data by an identical multiple to obtain zoomed-out left and right images, wherein the zoomed-out left and right images have a size of $\omega \times h$;

extracting and describing feature points of the zoomed-out left and right images by an oriented features from accelerated segment test (FAST) and rotated binary robust independent elementary features (BRIEF) (ORB) algorithm to obtain extracted feature points;

eliminating mismatched feature points of the zoomed-out left and right images by an improved grid-based motion statistics (IGMS) algorithm to obtain final matching points;

calculating average coordinate differences $P_x$, $P_y$ of the final matching points of the zoomed-out left and right images;

converting the average coordinate differences into the image parallaxes $aP_x, bP_y$; and transmitting the image parallaxes to the binocular camera in real time to control the offsets of left and right cameras of the binocular camera in directions x, y; wherein $$\omega = \frac{W}{a}, h = \frac{H}{b};$$

W×H is a size of original images; a and b are a zoom factor of a width and a zoom factor of a height of images, respectively;

wherein, the IGMS algorithm specifically comprises:

performing high-quantity matching on the zoomed-out left and right images by using a brute force (BF) matching algorithm based on the extracted feature points;

roughly eliminating the mismatched feature points by primarily using a grid-based motion statistics (GMS) algorithm, and selecting first n matching points with a high matching degree; and finely eliminating the mismatched feature points in the first n matching points by secondarily using the GMS algorithm, wherein 10≤n≤20;

the display module is configured to generate display data based on the binocular image data and display the display data through a display device for viewing with 3D glasses;

the operating microscope optical system is configured to perform an adjustment based on the control instructions;

the industrial I/O control card is configured to receive a switch quantity signal of the control module, and the industrial I/O control card feeds back the switch quantity signal to the image processing module in real time to control an operation and a stop of the image processing module;

wherein only when the pedal switch module controls the operating microscope optical system to execute the first type of control instructions, the industrial I/O control card receives a signal of the pedal switch module, activates the image processing module to process acquired images in real time, adjusts the offsets of the binocular camera after the image parallaxes are obtained, and transmits images acquired by the binocular camera after the image parallaxes are adjusted to the display module in real time for display; and when a switch of the pedal switch module is turned off, the industrial I/O control card receives a stop signal from the pedal switch module, and transmits the stop signal to the image processing module to stop adjusting the image parallaxes to ensure absolute safety during an operation, wherein the switch of the pedal switch module is configured to control the operating microscope optical system to execute the first type of control instructions.

2. The shutter type adaptive 3D display system based on the medical microscopic imaging according to claim 1, further comprising shutter type 3D glasses; wherein the display device is a shutter type 3D display screen.

3. The shutter type adaptive 3D display system based on the medical microscopic imaging according to claim 1, wherein the directional pedals comprise a moving-up pedal, a moving-down pedal, a translating-left pedal, a translating-right pedal, a translating-forward pedal and a translating-backward pedal; and the focusing pedals comprise a zooming-in pedal and a zooming-out pedal.

4. The shutter type adaptive 3D display system based on the medical microscopic imaging according to claim 1, wherein the display module generates the display data based on the binocular image data and displays the display data through the display device for viewing with the 3D glasses by a method comprising:

compressing the left and right images in the binocular image data by half in a width direction to fully fill left and right screens of the display device, respectively.

* * * * *